United States Patent [19]

Baffoni

[11] Patent Number: 5,530,212

[45] Date of Patent: Jun. 25, 1996

[54] MULTIPLE PHASE STETHOSCOPE

[76] Inventor: Frank A. Baffoni, 65 Ann Dr., East Greenwich, R.I. 02818

[21] Appl. No.: 440,482

[22] Filed: May 12, 1995

[51] Int. Cl.⁶ ....................................................... A61B 7/02
[52] U.S. Cl. ................................................................ 181/131
[58] Field of Search .................................... 181/131, 137; 381/67

[56] References Cited

U.S. PATENT DOCUMENTS

| | | | |
|---|---|---|---|
| 875,795 | 1/1908 | Fosgate | 181/131 |
| 2,389,868 | 11/1945 | Olson | 181/131 |
| 3,910,376 | 10/1975 | Azneer | 181/131 |
| 3,938,615 | 2/1976 | Bodenger | 181/131 |
| 4,270,627 | 6/1981 | Hill | 181/131 |
| 4,347,911 | 9/1982 | Bertagna et al. | 181/130 |
| 4,387,784 | 6/1983 | Hill | 181/131 |
| 4,776,426 | 10/1988 | Kazama | 181/131 |

Primary Examiner—Khanh Dang
Attorney, Agent, or Firm—Hale and Dorr

[57] ABSTRACT

A multiple phase stethoscope has a chest piece with a plurality of diaphragms and an equal plurality of sound compartments. Sound is carried from each of these compartments through a separate lumen, the plurality of lumens making up a tube assembly. The lumens are at least partially separated from each other by a flexible membrane which serves as a transducer to convert acoustic energy into mechanical motion, thus allowing the sound in the lumens to be combined. One of the lumens is open to the atmosphere through ear pieces, while the other lumen is sealed with a material and/or pressure different from the ambient environment. The geometry of the diaphragms, the compartments, and the lumens; the materials used for the flexible membrane in the lumens; and the pressure of the material in the lumens are all selected to enhance and/or attenuate at least a part of a frequency spectrum of the sounds. If two outer lumens are provided and are different around branches leading to the separate ear pieces, a stereophonic effect is created. This effect can be obtained by altering materials or geometry, e.g., by spiraling the outer lumen around the branches at different angles.

31 Claims, 6 Drawing Sheets

MULTIPLE PHASE STETHOSCOPE

FIELD OF THE INVENTION

This application relates to stethoscopes.

BACKGROUND OF THE INVENTION

Stethoscopes are used by physicians to listen to sounds produced in the human body, such as sounds from the lungs or the heart. A typical stethoscope has a chest piece, a tube, and ear pieces. The chest piece encloses a sound chamber and has a diaphragm. When placed against a patient, the diaphragm vibrates, thus creating sound in the sound chamber. The tube extends into the sound chamber and carries the sound to the ear pieces for the user to hear the sounds.

Some attempts have been made to improve the reception and expand the options of this typical stethoscope. Kazuma, U.S. Pat. No. 4,776,426, discloses a chest piece that is divided into two equally sized, semi-circular diaphragms and has two sound receiving chambers. Each chamber is separately coupled through a tube to one of the right and left ear tubes. This stethoscope purportedly provides stereophonic effect and more sensitive reception.

Hill, U.S. Pat. Nos. 4,270,627 and 4,387,784, discloses a stethoscope that has two resonant cavities and a switch for the user to select one or neither of these cavities. In these two patents, the resonant cavities are described as being designed to amplify a certain frequency range, while also venting pressure waves through openings into the ambient environment.

SUMMARY OF THE INVENTION

A stethoscope according to the present invention improves the ability to hear sounds from auscultation by enhancing and/or attenuating the sounds at desired frequencies, thus improving the ability of health care professionals to make accurate diagnoses. This improved ability is accomplished with a multiple phase stethoscope design, wherein sound from auscultation is received by a plurality of separate lumens and wherein sound in one lumen affects the sound in another lumen to selectively enhance and/or attenuate a desired frequency spectrum.

The stethoscope of the present invention has a chest piece with a plural number of sound compartments, and a plural number of diaphragms corresponding to the number of sound compartments. The diaphragms are preferably coplanar and concentric or coannular relative to each other. In an embodiment in which there are two diaphragms and two sound compartments, preferably, one diaphragm and one compartment are circular, and the other diaphragm and the other compartment are annular. In an embodiment with three lumens, two are preferably semi-annular, and one is circular. In this case, the lumens are still all considered coaxial based on the common axis for the radius or radius of curvature.

A tube assembly has a plurality of lumens, and preferably has at least as many lumens as the chest piece has diaphragms and sound compartments. The lumens are preferably coaxial relative to each other, and each extends into one of the sound compartments to receive and channel sounds. One of the lumens is open to the ambient environment through both ear pieces, while another of the lumens, preferably an outer lumen, is filled with a material that is sealed from the ambient environment; i.e., while a first lumen is effectively filled with air at one atmosphere, a second lumen is preferably filled with a material different from air and/or pressurized to a pressure other than one atmosphere. The material and the pressure of the second lumen at least partially determine whether a desired frequency range of the sound is enhanced or attenuated.

The lumens are separated, in whole or in part, by a thin flexible membrane that serves as a transducer which converts acoustic energy from a second sealed lumen into mechanical motion, thus causing the sounds in the second lumen to affect sounds in the first lumen. If there are two concentric lumens, the membrane defines the boundary between the lumens; and if there are three or more, some lumens may be separated from each other through other flexible or non-flexible partitions. The membrane is preferably made from a plastic, such as polypropylene.

If the membrane (or the combination of the membrane and the material in the sealed lumen) does not have sufficient structural strength, the membrane may be provided with a support system which maintains the stability of the membrane while allowing the membrane to remain flexible. The support system includes a support grid on a surface of the membrane, and rigid radial support pieces extending across the second lumen. The support pieces have circumferential openings for allowing a fluid, such as a gas, liquid, gel, or semisolid, to flow in the second lumen, thus preventing phase differences in portions of the second lumen.

The lead or lag in phase of the sound in the second lumen relative to the first can be advantageously controlled by careful selection of at least one of geometry, materials, and/or pressures. Similarly, the material and pressure in the second lumen can effectively serve as a high or low pass filter. Under either effect, the sound in the second lumen affects the sound in the first lumen to selectively enhance and/or attenuate certain frequencies or components of the sound that is heard by the user.

In other embodiments, the diaphragm and chest piece compartment are divided into three or more portions, and three or more corresponding lumens are provided. In one such embodiment, the inner diaphragm and inner lumen are circular in cross-section, while the outer diaphragms and two outer lumens are each semi-annular in cross-section. In this case, the outer lumens are each sealed and can be filled with different materials, e.g., a liquid in one and a gas in the other.

In these embodiments, a first lumen of the stethoscope splits into two branches, each of which extends to an ear piece. To produce a stereophonic effect in which each ear simultaneously receives a different signal (e.g., different in amplitude or phase), respective outer lumens around each branch are configured differently in at least one of material or geometry. The geometry can be different in one or more ways, e.g., a diameter of the outer lumen around one branch can be different from the diameter around the other branch; or two outer lumens can have spiral configurations around the branches of the first lumen such that an angle of the spiral can be made different for each branch. The material used to make the membrane or the outer cover can also be different for the outer lumen at portions around the different branches. Such differences in geometry and/or material cause the outer lumen to affect differently the sound in each of the branches, thus producing the stereophonic effect.

The multiple phase design of the present invention improves the detected sound by selectively enhancing or attenuating detected sounds based on at least one of the geometric configurations, materials, and pressures of the various components. The stethoscope according to the present invention preferably has a size that is similar to typical stethoscopes that are currently used, and does not require any parts to be moved by the user or any electrical amplification to improve the reception of sounds in a desired frequency spectrum. Other features and advantages will be apparent from the following detailed description and from the claims when read in conjunction with the drawings.

DETAILED DESCRIPTION

Figure 1:
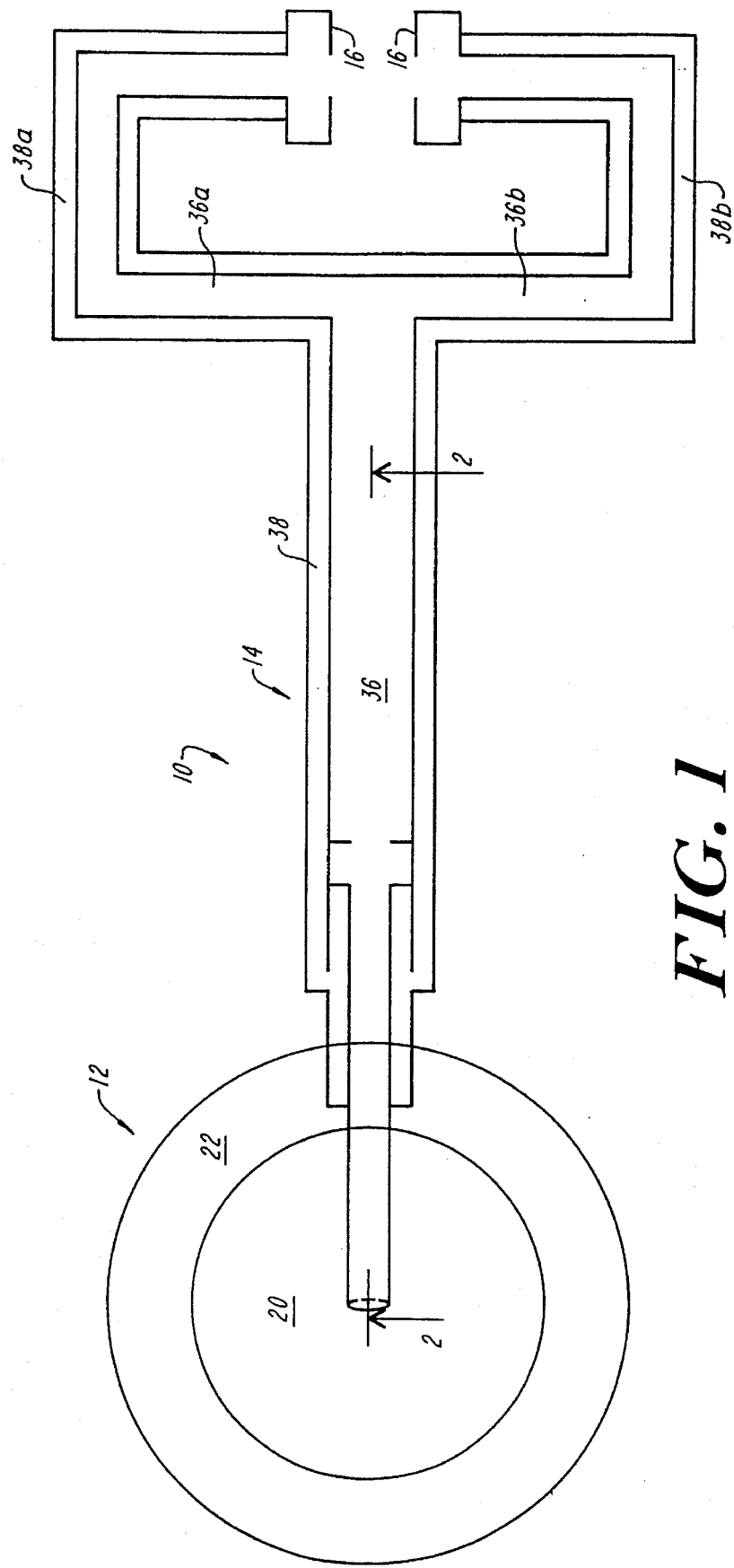
FIG. 1 is a schematic representation of a plan view of a stethoscope according to the present invention.
Figure 2:
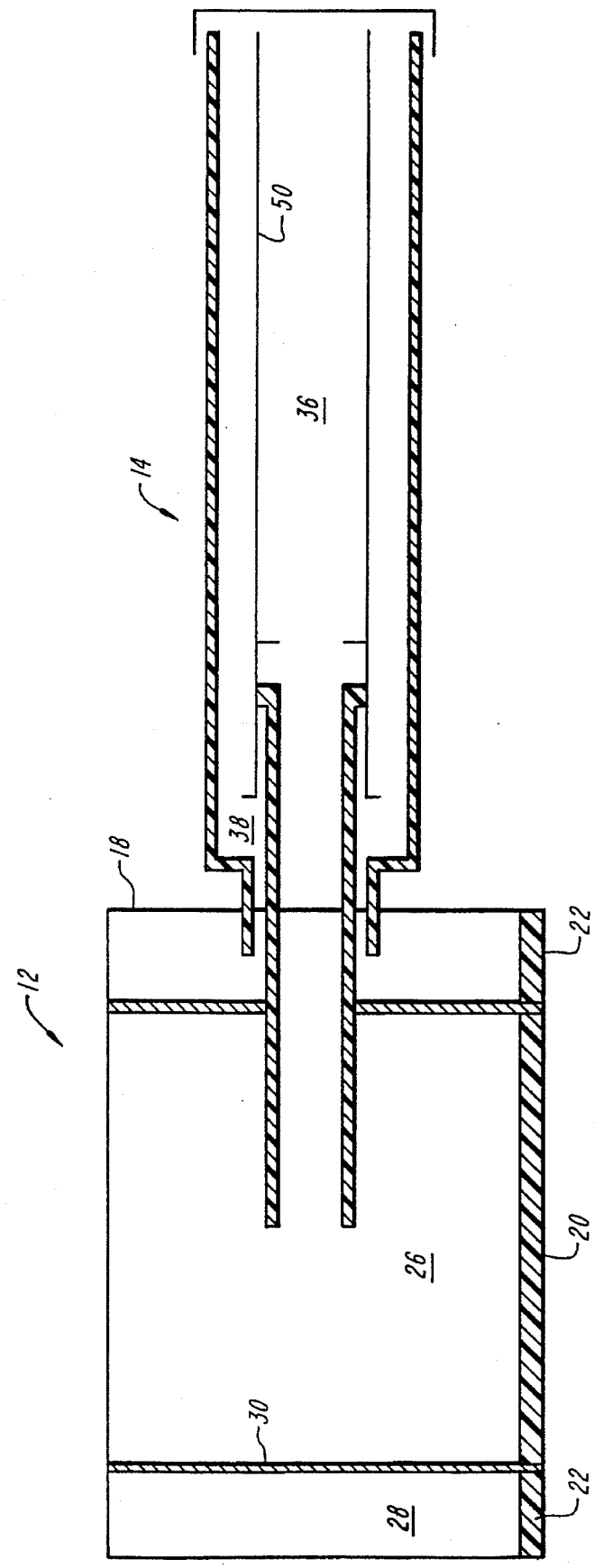
FIG. 2 is a partial cross-sectional view of the stethoscope of FIG. 1, taken through section lines 2—2.

Referring to FIGS. 1 and 2, a stethoscope 10 has a chest piece 12 for detecting sounds from a patient, a tube assembly 14 coupled to the chest piece for channeling the detected sounds, and ear pieces 16 through which a user, typically a physician or nurse, hears the detected sounds.

Chest piece 12 has a housing 18 that encloses sound compartments 26, 28, which are divided by a cylindrical partition 30. On one otherwise open side of housing 18 are a circular inner diaphragm 20 and an annular outer diaphragm 22 that is concentric with inner diaphragm 20. When the chest piece is placed against a patient's chest or back, each of the diaphragms vibrates, thus creating sounds in the respective sound compartment 26, 28.

Tube assembly 14 has two lumens 36, 38 that extend into housing 18. These lumens are coaxial and include a circular inner lumen 36 and an annular outer lumen 38. Lumens 36, 38 are acoustically coupled to the inner and outer compartments, respectively, for channeling sounds: outer compartment 28 isolates sound acquired by outer diaphragm 22 and channels the acquired sound to outer lumen 38; and inner compartment 26 isolates sound from inner diaphragm 20 and channels the acquired sound to inner lumen 36.

Inner lumen 36 splits into first and second branches 36a, 36b, each of which is open to the ambient environment through one of ear pieces 16. Thus, inner lumen 36 is generally filled with air at one atmosphere. The ear pieces are open to inner lumen 36 in that there is a continuous air path between the ear pieces and the inner lumen. Outer lumen 38 also splits into branches 38a, 38b, each of which is coaxial with a respective branch 36a, 36b of inner lumen 36. Alternatively, for simpler construction, the outer lumen can extend up to the portion where inner lumen 36 splits, and the rest of inner lumen 36 can be covered with a solid cover.

Figure 3:
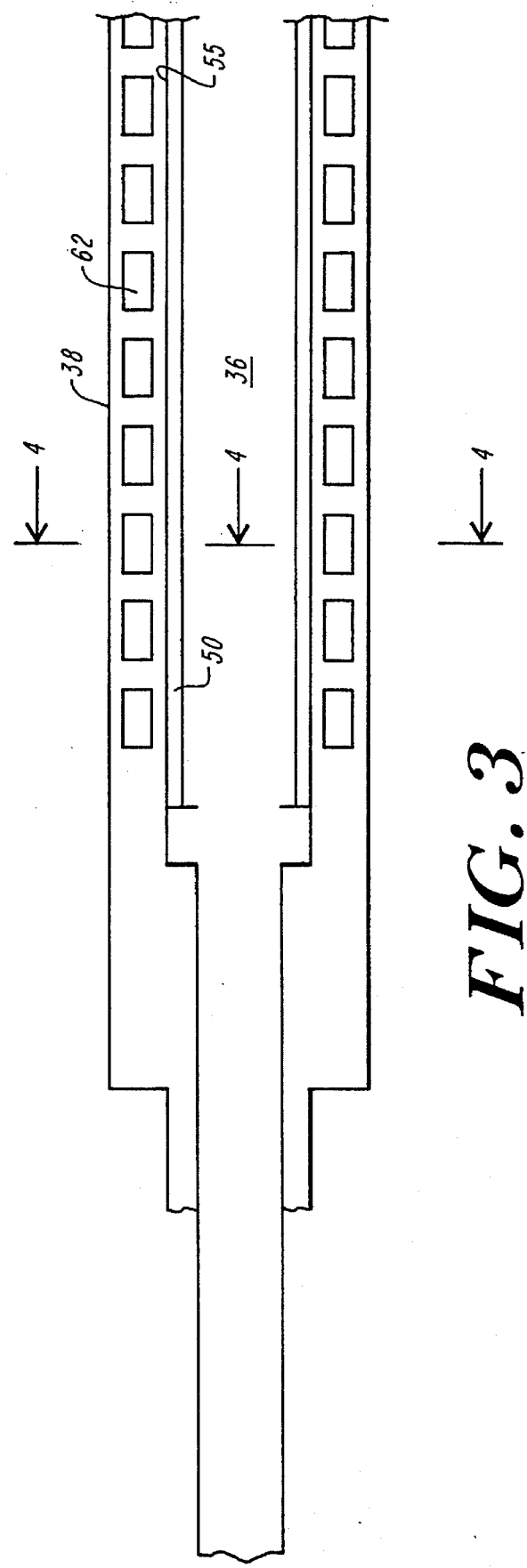
FIG. 3 is a schematic diagram of a portion of a tube assembly showing a structural support system.
Figure 4:
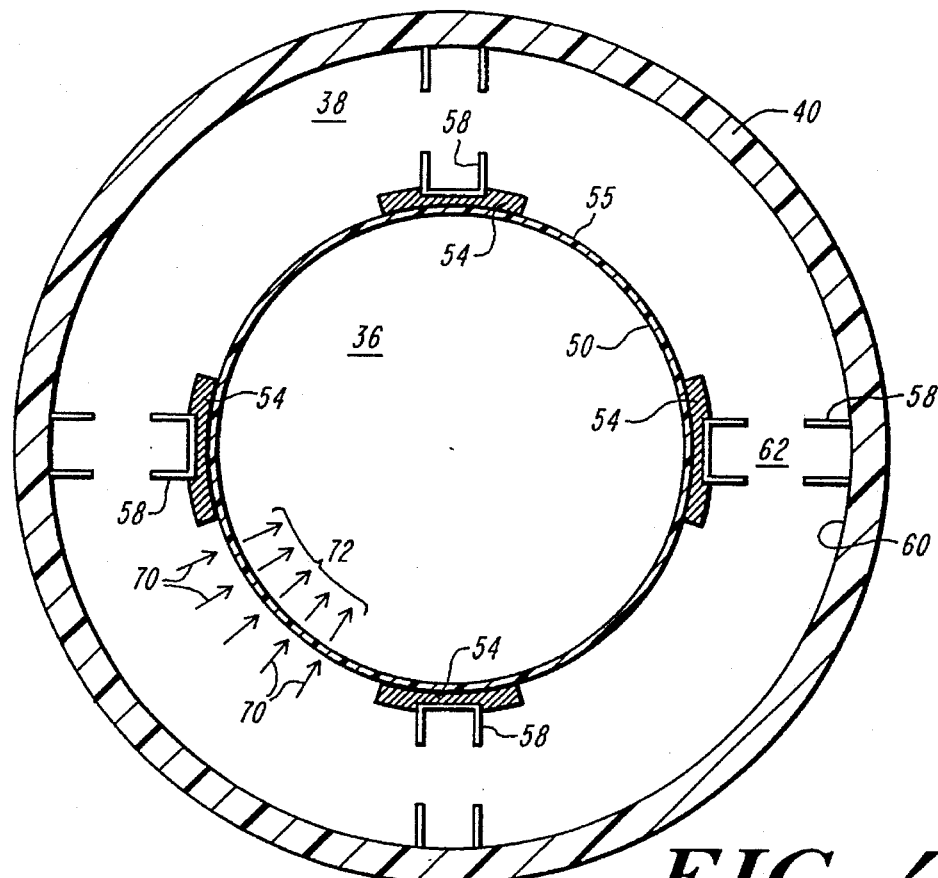
FIG. 4 is a cross-sectional view taken along section lines 4—4 of FIG. 3.
Figure 5:
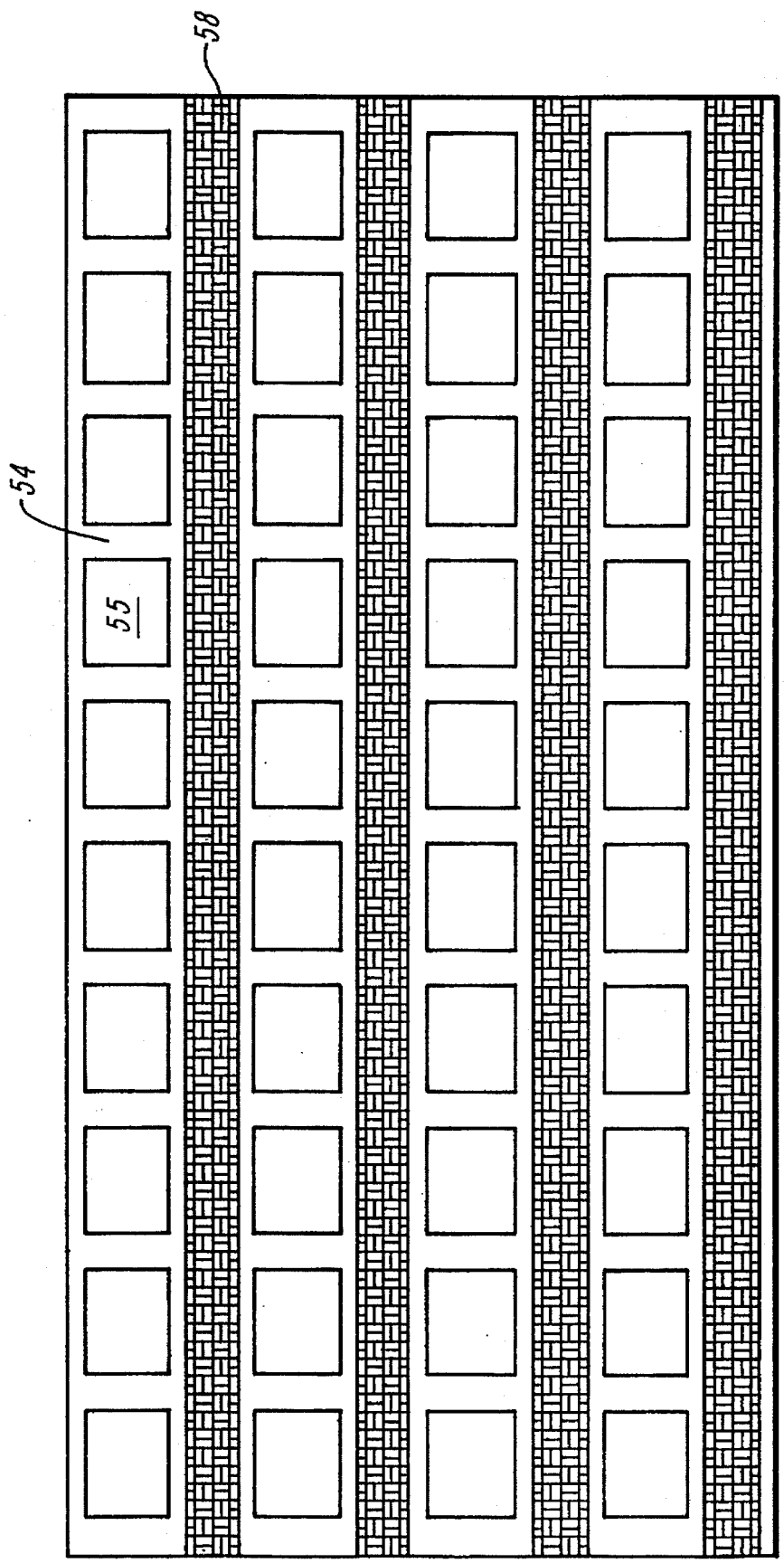
FIG. 5 is a plan view of a flexible membrane and membrane support system cut longitudinally and flattened.

So that the sound carried in the first and second lumens will be different, and thus will have different characteristics, outer compartment 28 and outer lumen 38 are preferably sealed relative to the inner lumen and hence to the ambient environment. The second lumen is filled with a fluid material, such as a gas, liquid, gelatinous, or semisolid material. The material in outer lumen 38 may also be pressurized or a vacuum may be drawn so that the material is at a pressure that is different from the ambient environment, which is generally air at one atmosphere. Accordingly, while inner lumen 36 has the ambient environmental conditions of air at one atmosphere of pressure, outer lumen 38 preferably is under different conditions in that it is either not filled with air, is not at one atmosphere, or both. Referring also to FIGS. 3–5, outer lumen 38 has at its outer diameter a cover 40, preferably made of a plastic, rubber, or synthetic rubber, to protect the stethoscope from the outside environment. A spring member (not shown) is preferably provided between the branches for biasing the branches and ear pieces together. The spring member holds the ear pieces tightly to the user's ears, and allows the stethoscope to be held securely around the user's neck when the stethoscope is not being used.

Since the sounds in the two lumens differ and travel under different conditions depending on the geometry, materials, and pressure, the differences in the sound in the outer lumen can be used to affect the sound in the inner lumen. Thus, if the outer lumen passes relatively higher or lower frequencies, or has a particular phase delay, that sound in the outer lumen can affect the sound in the inner lumen to enhance or suppress certain aspects of the sounds in the inner lumen.

Lumens 36, 38 are separated by a flexible membrane 50 which is responsive to the sound in the two lumens so that, e.g., the sound in the outer lumen affects sound in the inner lumen. While sound traveling through inner lumen 36 is directly coupled through an air path to ear pieces 16, sound traveling in the outer lumen 38 does not pass to the ear but rather causes movement of membrane 50, in a direction generally perpendicular to the membrane along the entire length of the membrane. Thus the sound carried in the outer lumen 38 moves across membrane 50 as indicated by arrows 70 (FIG. 4) and flexes membrane 50 as indicated by arrows 72 (for convenience, the arrows are only shown for a portion of the circumference of the membrane, but the flexing would occur around the circumference). Membrane 50, which forms at least part of a common wall between the lumens, thus serves effectively as a transducer in converting acoustic energy in the outer lumen into mechanical motion of the membrane, which in turn affects the sound in the inner lumen. Depending on the selection of pressure and material in the outer lumen, enhancement and/or attenuation of the amplitude of the sound within inner lumen 36 can be attained For example, if the outer lumen moves the membrane at low frequency, such movement can enhance lower frequencies in the inner lumen relative to higher frequencies.

Membrane 50 is made of a material, such as polypropylene, that is both flexible and can sufficiently seal lumens 36, 38 to prevent the material in outer lumen 38 from mixing with the air in inner lumen 36. The choice of material for membrane 50 also helps cause the amplitude of a desired frequency spectrum in the inner lumen to be enhanced or attenuated.

Stethoscope are often worn around the neck, but they also can fall, get stuffed into a pocket, and be otherwise subject to physical abuse. The design of the stethoscope needs to take into consideration such physical stress. If the material in outer lumen 38 is a thick liquid or is a semisolid, the combination of the material and membrane 50 may be sufficient to support the membrane. But if the material does not offer adequate support, a membrane support system is provided to give additional support. The support system allows membrane 50 to flex and transmit sound along its length, while also allowing it to serve as a cylindrical barrier between the lumens.

Referring to FIGS. 3–5, the support system has a membrane support grid, which preferably covers the membrane's outer surface 55 to a minimal degree necessary to give sufficient stability. The support grid includes thin, elongated members 54 (not shown in FIG. 3), which extend longitudinally along surface 55. There are preferably four members 54 which are equally sized and arranged around the outer circumference of lumen 36. Coupled to members 54 are rigid grid connecting posts 58 which radially traverse the outer lumen and are attached to an inner surface 60 of outer lumen 38. Connecting posts 58 are perforated by an axial array of circumferential, rectangular openings 62 that allow for consistency in the sound and consequently prevents isolation of the sound in different parts of the outer lumen and hence phase differences in the outer lumen.

Figure 6:
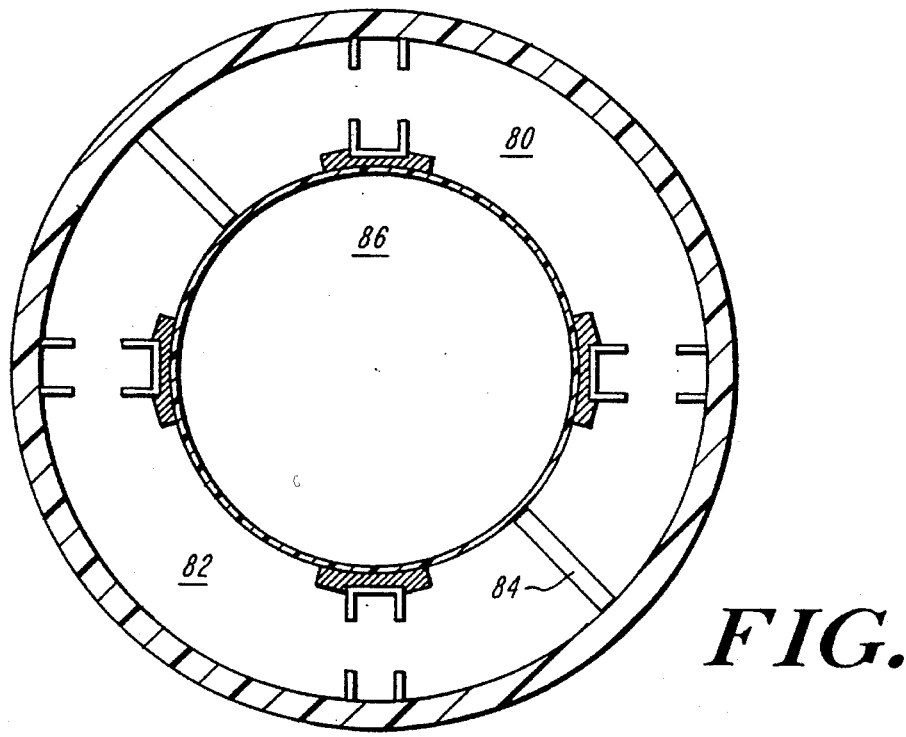
FIG. 6 is a cross-sectional view of another embodiment of the present invention and is analogous to FIG. 4.

While the present invention has been described as having two diaphragms and two lumens, more lumens and diaphragms can be provided. Referring to FIG. 6, in another embodiment of the present invention, the outer annular diaphragm is further divided by a partition so that there are two semi-annular diaphragms and sound compartments (not shown). Two outer lumens 80, 82 are semi-annular and are divided by a divider 84, while an inner lumen 86 is cylindrical. The support grid is generally similar to that described in conjunction with FIGS. 3–5. In addition, multiple lumens can be provided for one diaphragm.

Figure 7A:
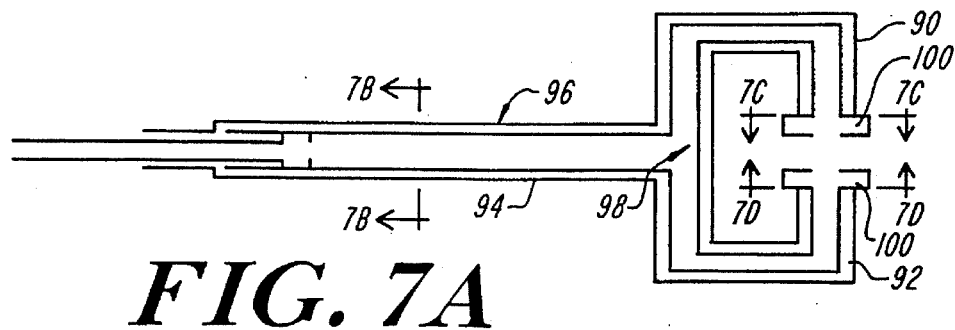
FIG. 7(a) is a schematic plan view of a tube assembly according to another embodiment of the present invention.
Figure 7B:
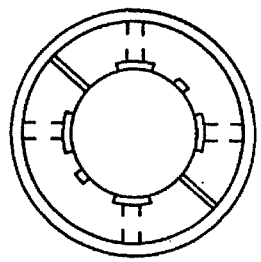
FIGS. 7(b)–7(d) are cross-sectional views of the stethoscope of FIG. 7(a) taken through section lines b–d, respectively.

Referring also to FIGS. 7(a)–7(f), in the triple lumen (three phase) construction of FIG. 6, divider 84 has a longitudinal spiral in branches 90, 92. In FIG. 7(b), portion 94 of tube assembly 96 refers to the part between the chest piece (not shown) and a split section 98 of the tube assembly. In portion 94, there is no spiral in the outer lumens.

Figure 7C:
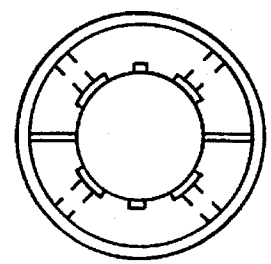
Figure 7D:
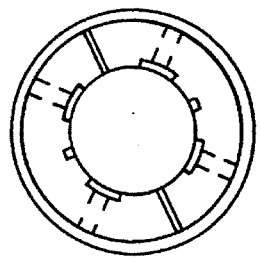
Figure 7E:
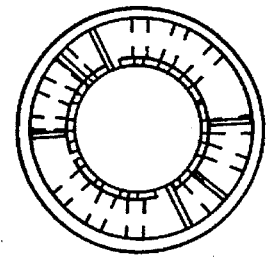
FIGS. 7(e)–7(f) are composite cross-sectional views of the stethoscope of FIG. 7(a).
Figure 7F:
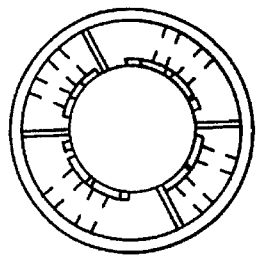

As shown in FIGS. 7(c) and 7(d), the outer lumens have a spiral so that they are rotated, for example by −45° and +22.5°, respectively, relative to the outer lumen's position in FIG. 7(b) at portion 94 of the tube assembly. The spiral is gradual from split section 98 out to ear pieces 100. FIGS. 7(e) and 7(f), which superimpose FIG. 7(b)–7(d) and FIGS. 7(c)–7(d), respectively, illustrate this spiraling.

The spiral changes the geometry of the outer lumen in each branch by providing more length and surface area between the lumens, thus providing another variable factor for adjusting the sound. Because the spiraling portion of the two outer lumens are different from split section 98 to the ear pieces, the sounds in the inner lumen in branches 90, 92 are affected in a different manner. This difference provides stereophonic imaging of the sound because at least one sound component, such as phase or amplitude, is different in each branch.

Stereophonic imaging can also be produced by configuring the outer lumens differently by altering the material or other geometric aspects of the outer lumen. The geometry can be different by altering the diameter of the outer lumen around one branch relative to the other, or by making the length different. The materials can be different by using a different membrane, support grid, or outer cover for the portions of the outer lumen around the two branches.

If further diaphragms are provided, it is expected that all of the diaphragms will be generally coplanar with respect to each other so that each of the separate diaphragms is receiving sound from the patient at the same time.

Having described embodiments of the present invention, it should be apparent that other variations and modifications can be made without departing from the scope of the appended claims. Altering the geometric characteristics or materials used for the diaphragms sound compartments, lumens, membrane, grid, and ear pieces can change the frequency characteristics of a stethoscope according to the present invention. The lumens can be arranged in different configurations, such as a side-by-side arrangement.

What is claimed is:

1. A stethoscope comprising:

a chest piece having a housing enclosing first and second sound compartments, the sound compartments being separated from each other;

a tube assembly coupled to the chest piece and including first and second lumens, the first lumen being coupled to receive sounds from the first compartment and the second lumen being coupled to receive sounds from the second compartment;

a flexible member intermediate and forming at least part of a common wall of said first and second lumens, the member being responsive to sound in the second lumen such that sound in the second lumen affects sound in the first lumen; and a first ear piece open to the first lumen.

2. The stethoscope of claim 1, wherein the first and second lumens are coaxially disposed.

3. The stethoscope of claim 1, further including a support system for supporting the membrane while allowing the membrane to remain sufficiently flexible so that the sound in the second lumen affects the sound in the first lumen.

4. The stethoscope of claim 3, wherein support members extend longitudinally along a surface of the membrane.

5. The stethoscope of claim 1, wherein the first and second compartments are concentric relative to each other.

6. The stethoscope of claim 1, wherein the first lumen is filled according to the ambient environment and the second lumen is sealed with at least one of a material and a pressure different from the ambient environment, and wherein the first lumen is open to the first ear piece.

7. The stethoscope of claim 6, wherein the second lumen is filled with a gas other than air.

8. The stethoscope of claim 6, wherein the second lumen is filled with a liquid.

9. The stethoscope of claim 6, wherein the pressure of the material in the second lumen is different from ambient environmental pressure.

10. The stethoscope of claim 9, wherein the material in the second lumen is air.

11. The stethoscope of claim 6, wherein the pressure is the same as the ambient environment and the material is different from the ambient environment.

12. The stethoscope of claim 6, wherein the material is one of a gel and a semisolid.

13. The stethoscope of claim 1, further including a third sound compartment and a third lumen coupled to receive sounds from the third diaphragm.

14. The stethoscope of claim 13, wherein the second and third sound compartments are semi-annular in cross-section.

15. The stethoscope of claim 14, wherein the second and third lumens are divided by a partition extending along a length between the second and third lumens.

16. The stethoscope of claim 15, wherein the partition has a spiral over at least a portion of its length, wherein an angle of spiral is different at portions of the stethoscope corresponding to the different ear pieces, the different angles creating a stereophonic effect.

17. The stethoscope of claim 1, further including a second ear piece, the first lumen branching into first and second branches to the first and second ear pieces, respectively, the second lumen having first and second portions about respective first and second branches, wherein the first and second portions are configured differently to provide a sterophonic effect.

18. A stethoscope comprising:
   a chest piece having a housing enclosing first and second sound compartments, the sound compartments being separated from each other;
   a tube assembly including a first and second lumens for carrying first and second sounds, the first lumen being acoustically coupled to the first compartment, the second lumen being acoustically coupled to the second compartment, the material in the second lumen being sealed relative to material in the first lumen; and
   ear pieces having an open air path to the first lumen and not to the second lumen.

19. The stethoscope of claim 18, wherein the second lumen is sealed with one of a material and a pressure in the second lumen is different from one of a respective material and a pressure in the first lumen.

20. The stethoscope of claim 19, wherein the second lumen is filled with a gas other than air.

21. The stethoscope of claim 19, wherein the second lumen is filled with a liquid.

22. The stethoscope of claim 19, wherein the second lumen is filled with one of a gel and a semisolid material.

23. The stethoscope of claim 19, wherein the pressure of the material in the second lumen is different from the pressure in the first lumen.

24. The stethoscope of claim 23, wherein the second lumen is filled with air.

25. The stethoscope of claim 18, wherein the first and second lumens are separated by a flexible membrane that allows sound in the second lumen to affect sound in the first lumen.

26. The stethoscope of claim 25, wherein the lumens are concentrically and coaxially arranged.

27. A stethoscope comprising:
   a chest piece having a first diaphragm and a second diaphragm, the second diaphragm being concentric relative to the first diaphragm;
   a tube assembly including a first lumen and a second lumen for carrying first and second acoustic signals, the first lumen being open to the first diaphragm and the second lumen being open to the second diaphragm, wherein the second lumen at least partially surrounds the first lumen such that the first and second lumens are concentrically and coaxially arranged; and
   an ear piece having an open air path to one of the first and second lumens.

28. The stethoscope of claim 27, wherein the tube assembly further includes a third lumen, wherein the second and third lumens form at least part of a cylindrical annulus that is coaxial with the first lumen.

29. The stethoscope of claim 28, wherein the second and third lumens are divided at least in part by a partition having a longitudinal spiral configuration.

30. The stethoscope of claim 29, wherein the first lumen splits into first and second branches extending to first and second ear pieces, wherein an angle of spiral around the first branch is different from an angle of spiral around the second branch, thus crating a stereophonic effect.

31. The stethoscope of claim 27, wherein a material in the second lumen is sealed from the material in the first lumen.

* * * * *